(12) United States Patent
Bloemer et al.

(10) Patent No.: US 8,676,343 B2
(45) Date of Patent: Mar. 18, 2014

(54) MULTI-ELECTRODE LEADS FOR BRAIN IMPLANTATION

(75) Inventors: Frank Bloemer, Berlin (DE); Erhard Flach, Berlin (DE)

(73) Assignee: Biotronik SE & Co. KG (DE)

( * ) Notice: Subject to any disclaimer, the term of this patent is extended or adjusted under 35 U.S.C. 154(b) by 0 days.

(21) Appl. No.: 13/402,921

(22) Filed: Feb. 23, 2012

(65) Prior Publication Data

US 2012/0232629 A1 Sep. 13, 2012

Related U.S. Application Data

(60) Provisional application No. 61/451,126, filed on Mar. 10, 2011.

(51) Int. Cl.
*A61N 1/00* (2006.01)

(52) U.S. Cl.
USPC .......................................... 607/116

(58) Field of Classification Search
USPC .......................................... 607/116
See application file for complete search history.

(56) References Cited

U.S. PATENT DOCUMENTS

| | | | |
|---|---|---|---|
| 6,066,163 A | 5/2000 | John | |
| 6,304,784 B1 * | 10/2001 | Allee et al. | 607/116 |
| 6,343,226 B1 | 1/2002 | Sunde et al. | |
| 6,354,299 B1 | 3/2002 | Fischell et al. | |
| 6,368,147 B1 | 4/2002 | Swanson | |
| 6,454,774 B1 | 9/2002 | Fleckenstein | |
| 6,459,936 B2 | 10/2002 | Fischell et al. | |
| 6,463,328 B1 | 10/2002 | John | |
| 6,484,059 B2 | 11/2002 | Gielen | |
| 6,495,020 B1 | 12/2002 | Swanson | |
| 6,539,263 B1 | 3/2003 | Schiff et al. | |
| 6,560,472 B2 | 5/2003 | Hill et al. | |
| 6,587,724 B2 | 7/2003 | Mann | |
| 6,662,035 B2 | 12/2003 | Sochor | |
| 6,909,917 B2 | 6/2005 | Woods et al. | |
| 7,212,867 B2 | 5/2007 | Van Venrooij et al. | |
| 2002/0198446 A1 | 12/2002 | Hill et al. | |
| 2007/0027515 A1 * | 2/2007 | Gerber | 607/116 |
| 2007/0123765 A1 | 5/2007 | Hetke et al. | |
| 2011/0154655 A1 | 6/2011 | Hetke et al. | |

FOREIGN PATENT DOCUMENTS

WO WO 2007/042999 A2 4/2007

OTHER PUBLICATIONS

European Search Report, Application No. 12158192.0-1265, Jul. 7, 2012.

* cited by examiner

*Primary Examiner* — Christopher D Koharski
*Assistant Examiner* — Nadia Ahmad
(74) *Attorney, Agent, or Firm* — Craig A. Fieschko, Esq.; DeWitt Ross & Stevens S.C.

(57) ABSTRACT

A lead for use in Deep Brain Stimulation (DBS) and similar applications has a rigid lead tip with multiple electrodes thereon. The electrodes are formed by coating a lead tip core with a conductive material; selectively removing the conductive material to define the electrodes and conductive tracks leading therefrom; and then applying a layer of insulating material over the tracks to leave the electrodes exposed. Terminals are also left exposed on the tracks for connection to energy supply and/or data transmission lines. Such lines are preferably provided on or within a flexible lead body connected to the lead tip.

19 Claims, 2 Drawing Sheets

MULTI-ELECTRODE LEADS FOR BRAIN IMPLANTATION

CROSS-REFERENCE TO RELATED APPLICATIONS

This application claims priority under 35 USC §119(e) to U.S. Provisional Patent Application 61/451,126 filed 10 Mar. 2011, the entirety of which is incorporated by reference herein.

FIELD OF THE INVENTION

This document concerns an invention relating generally to electrodes suitable for implantation in the brain, and more specifically to multi-electrode leads suitable for use in Deep Brain Stimulation (DBS) and similar applications.

BACKGROUND OF THE INVENTION

The brain includes gray matter, primarily collections of neurons which serve to process information and generate responsive signals, and white matter, primarily axons which serve to communicate these signals between gray matter regions and more distant parts of the nervous system. It is well known that specific regions within the gray matter are associated with particular functions; for example, motor skills are primarily controlled by regions in the cerebral cortex, the cerebellum, and the basal ganglia. Thus, there is significant interest in delivering signals to different regions of the brain to modify the brain's activity, and/or in measuring and interpreting signals from different regions of the brain to allow the brain to communicate with external devices. As an example, in the developing field of DBS (Deep Brain Stimulation), therapeutic (micro) electrodes are implanted within the brain to deliver timed impulses to desired nerve centers to treat a variety of disorders, in particular motor disorders such as Parkinson's disease and dystonia. As another example, in the developing field of man-machine interfaces, electrode arrays are implanted in the brain and the signals measured therefrom may be used to control prostheses, communication devices, or other machines. Further details can be found, for example, in U.S. Pat. No. 6,066,163 to John, U.S. Pat. No. 6,343,226 to Sunde et al., U.S. Pat. No. 6,354,299 to Fischell et al., U.S. Pat. No. 6,368,147 to Swanson, U.S. Pat. No. 6,454,774 to Flechenstein, U.S. Pat. No. 6,459,936 to Fischell et al., U.S. Pat. No. 6,463,328 to John, U.S. Pat. No. 6,484,059 to Gielen, U.S. Pat. No. 6,495,020 to Swanson, U.S. Pat. No. 6,539,263 to Schiff et al., U.S. Pat. No. 6,560,472 to Hill et al., U.S. Pat. No. 6,662,035 to Sochor, U.S. Pat. No. 6,587,724 to Mann, U.S. Pat. No. 6,731,986 to Mann, and U.S. Pat. No. 6,909,917 to Woods, as well as the patents cited in (and citing to) these patents.

Typically, electrodes for the foregoing applications are situated on one or more small-diameter leads implanted within a patient's head, with each lead bearing multiple electrodes (usually 4 to 8 electrodes). In appropriate circumstances, the same electrodes can be used for delivery of stimulation as well as sensing of intracerebral signals, as by switching selected electrodes between connection to stimulation delivery systems and connection to sensing systems. The leads are typically cylindrical, and bear internal conductors connected to annular electrodes spaced along the length of the lead. Because of the small diameter of the lead (and the limited space for conductor cables therein), the number of electrodes that can be placed on a lead is limited. Additionally, the annular design of the electrodes can make it difficult to determine the orientation of measured signals and/or to direct stimulation to desired brain regions (e.g., in the technique known as "field steering" or "current steering," wherein different electrodes along a lead may take different roles as source electrodes and sink electrodes over time to determine optimal current paths for treatment). It would therefore be useful to have arrangements which allow electrodes to be placed along leads with greater density, and/or which allow better directional stimulation delivery and/or sensing ability.

SUMMARY OF THE INVENTION

The invention, which is defined by the claims set forth at the end of this document, is directed to multi-electrode leads, and methods for their manufacture, which at least partially alleviate the aforementioned problems. A basic understanding of some of the features of preferred versions of the invention can be attained from a review of the following brief summary of the invention, with more details being provided elsewhere in this document. To assist in the reader's understanding, the following review makes reference to the accompanying drawings (which are briefly reviewed in the "Brief Description of the Drawings" section following this Summary section of this document).

FIGS. 1A-1D schematically depict a preferred method for forming an exemplary multi-electrode tip 100 for a lead. In FIG. 1A, an elongated core 102 having a nonconductive exterior surface 104 is provided, with the core 102 having a length extending between a proximal end 106 and a distal end 108. The core 102 is preferably formed of an at least substantially rigid insulating or dielectric (and preferably biocompatible) material, such as an appropriate ceramic or polymer (e.g., polyethylene, polyurethane, silicone, or polyetherketone). The core's exterior surface 104 is then coated with an electrically conductive (and preferably biocompatible) material 110, as depicted in FIG. 1B. This material, which is preferably gold, platinum, iridium, wolfram or tantalum, can be applied by sputtering, deposition, plating, printing, or other appropriate methods to provide a conductive film or layer 110 having a desired thickness (typically less than 0.5 mm). Portions of the conductive layer 110 are then removed, as by use of chemical etching and/or laser removal, to define conductive tracks 112 on the core's exterior surface 104 (as in FIG. 1C). The conductive tracks 112 extend along the core's exterior surface 104 from locations nearer the core's proximal end 106, and terminate in electrodes 114 at locations nearer the core's distal end 108. FIG. 1D then shows this arrangement after a nonconductive outer layer 116 has been applied to the core 102 to cover the tracks 112 and adjacent portions of the core's exterior surface 104, but leaving the electrodes 114 exposed (as well as any desired terminals 118 at or near the core's proximal end 106). As an alternative, the nonconductive outer layer 116 can be applied over the entirety of the core 102, including the electrodes 114 and any terminals 118, and can be removed where desired to expose the electrodes 114 and terminals 118, again by methods such as chemical etching, the application of laser or other radiation, etc.

A (preferably flexible) lead body having conductors extending therein can then be joined to the proximal end 106 of the lead tip 100, such that the conductors are attached in electrical communication with the tracks 112 and their electrodes 114 (as by joining the conductors to the terminals 118 near the lead tip's proximal end 106). An exemplary arrangement of this nature is depicted in FIG. 2, wherein an electrode-bearing lead tip 200 similar to that of FIG. 1 has a somewhat conical proximal end 206 with exposed terminals 218, wherein each terminal 218 is in electrical communication with one of the electrodes 214 via conductive tracks (which are not visible in FIG. 2 because they are obscured by the insulating coating thereover). The proximal end 206 can be received within a mating socket 220 in a lead body 222, which is shown in cross-section such that some of the conductors 224 therein are visible, and can be fastened to the lead body 222 via welding, soldering, gluing, crimping, and/or other fastening arrangements such that each of the lead body's conductors 224 is in electrical communication with the terminals 218 of one or more of the conductive tracks of the lead tip 200 (and thus with the electrodes 214). A stimulation and/or measurement system at the proximal end of the lead body 222 (not shown) can therefore deliver stimulation or other signals to, or can convey signals from, the electrodes 214 via the lead body 222 and its conductors 224.

FIG. 3 shows an alternative arrangement wherein the lead body 322 bears a reduced number of conductors 324 (e.g., 2-4 conductors), thereby increasing the flexibility and reliability of the lead body 322, with a multiplexer 326 joining the conductors 324 to the tracks 312 of the electrodes 314 of the lead tip 300. One or more control leads (not shown) within the lead body 322 can then control the multiplexer 326 to switch the conductors 324 into connection with different tracks 312 and electrodes 314 at different times. Preferably, the multiplexer 326 is provided on a proximal end of the lead tip 300, and the lead body 322 is then connected to the lead tip 300 via soldering, welding, crimping, adhesives, and/or any other appropriate means of attachment such that its conductors 324 are operatively connected to the multiplexer 326.

The concepts of the foregoing methods and arrangements allow the generation of complex electrode geometries with little or no assembly. Electrodes can be specially sized, shaped, and placed to better fulfill stimulation and/or sensing functions, e.g., stimulation or "pace" electrodes can be sized larger than, and can be regularly distributed about, smaller measurement or "sense" electrodes (as in FIG. 1D, FIG. 2, and FIG. 3). Distributing electrodes both circumferentially and longitudinally along the lead tip allows a wide variety of current/field steering arrangements as different electrodes are chosen to serve as current sources and current sinks. Electrodes can also be formed with high density over the surface of the lead tip, as illustrated by the side elevational views of alternative exemplary lead tips 400A and 400B in FIGS. 4A and 4B (wherein tracks 412A/412B and electrodes 414A/414B are shown prior to application of an insulating coating), with FIG. 4A illustrating ring electrodes 414A closely spaced longitudinally along the lead tip 400A, and FIG. 4B illustrating partial ring electrodes 414B closely spaced both longitudinally and circumferentially along the lead tip 400B.

In use, the lead (i.e., the lead tip and the proximal lead body) can be situated within a patient's brain, and the electrodes can be used to deliver electrical stimulation to the brain, and/or to sense the brain's electrical activity. Where electrodes are arrayed about the circumference and/or length of the lead tip (as in FIG. 1D, FIG. 2, FIG. 3, and FIGS. 4A-4B), field/current steering can be performed by switching between different electrodes to vary their roles as current sources and current sinks, such that current is delivered between different pairs of electrodes at different times.

Further versions, features, advantages, and objects of the invention will be apparent from the remainder of this document in conjunction with the associated drawings.

DETAILED DESCRIPTION OF EXEMPLARY VERSIONS OF THE INVENTION

Expanding on the discussion above, the lead tip may assume virtually any configuration, such as a cylindrical shape (as depicted in the accompanying drawings), a flattened cylindrical shape (e.g., an oval cross-section), or on the form of polygonal beams (e.g., beams having triangular, square, or other cross-sections). Substantially flat rectangular cross-sections are also possible. In this case, the core of the lead tip (and possibly the "spine" of the adjacent lead body) might be formed of insulating sheet-like material (e.g., a polymer strip), with tracks/electrodes and insulating layers (and the conductors of the lead body) subsequently being deposited on, printed on, or otherwise applied to one or both sides of the sheet. A similar approach can be taken for cores and lead bodies formed in non-sheetlike shapes, e.g., in the form of rods or beams. It should be apparent from the foregoing discussion that the lead tip and lead body need not be separately formed, though it is preferred that the lead tip be rigid and that the lead body be flexible. Thus, if a single-piece lead tip core and lead body spine are used, a stiffening element might be added to impart rigidity to the core of the lead tip, or the core of the lead tip might be configured or otherwise formed to have greater rigidity than the adjacent length which is to define the lead body.

Figure 1A:
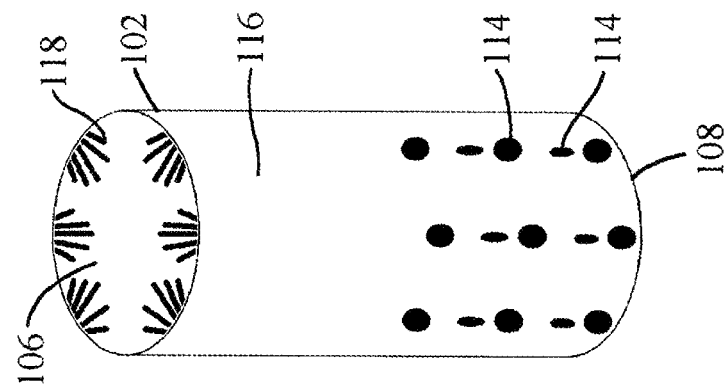
FIGS. 1A-1D schematically illustrate a method of manufacturing an exemplary electrode-bearing lead tip 100 wherein an insulating core 102 (FIG. 1A) is coated with a conductive film or layer 110 (FIG. 1B), which is then selectively removed to define conductive tracks 112 extending between proximal terminals 118 and distal electrodes 114 (FIG. 1C), and wherein the conductive tracks 112 are then covered with an insulating film or layer 116 such that only desired portions of the electrodes 114 and terminals 118 are left exposed (FIG. 1D).
Figure 1B:
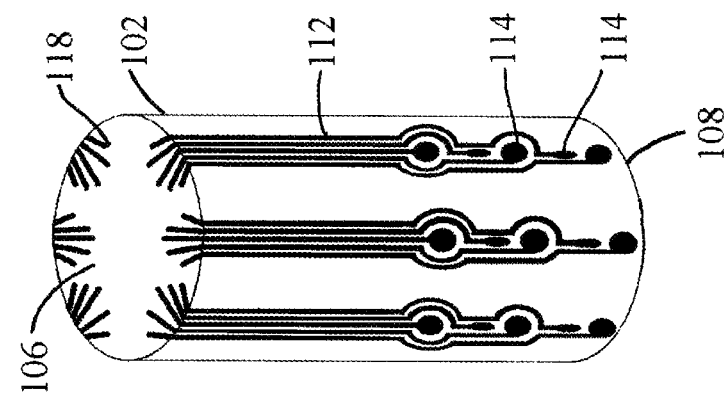
Figure 1C:
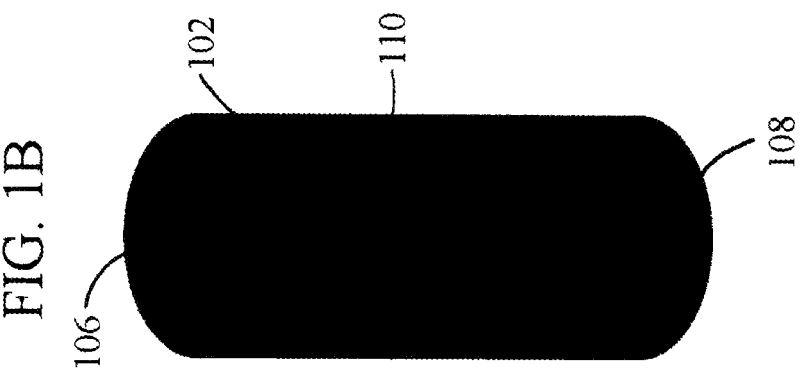
Figure 1D:
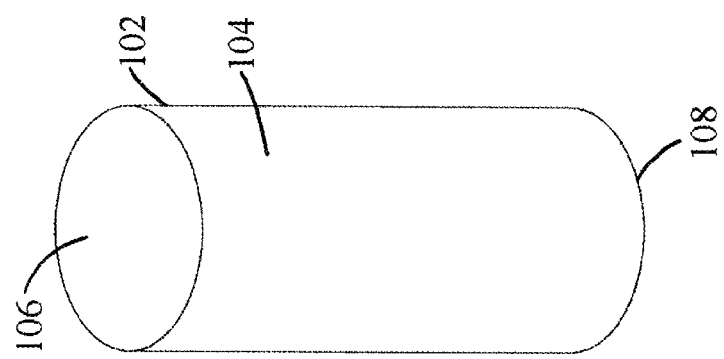
Figure 2:
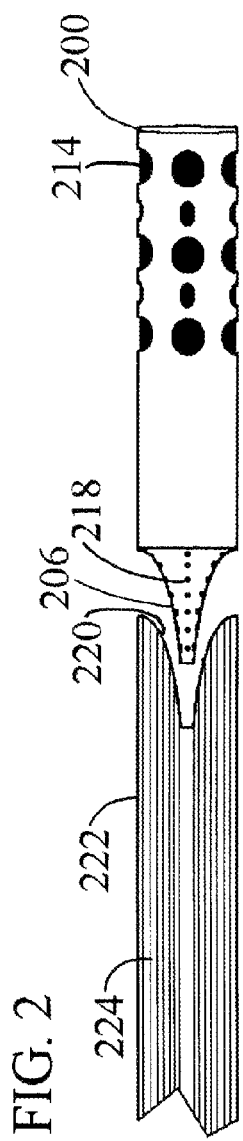
FIG. 2 schematically illustrates an electrode-bearing lead tip 200 similar to that of FIG. 1D, but having a proximal male plug 206 bearing the terminals 218 for the electrodes 214, with the male plug 206 being received in a socket in a flexible lead body 222 (shown in cross-section), whereby conductors 224 within the lead body 222 are in electrical communication with the electrodes 214 after assembly.
Figure 3:
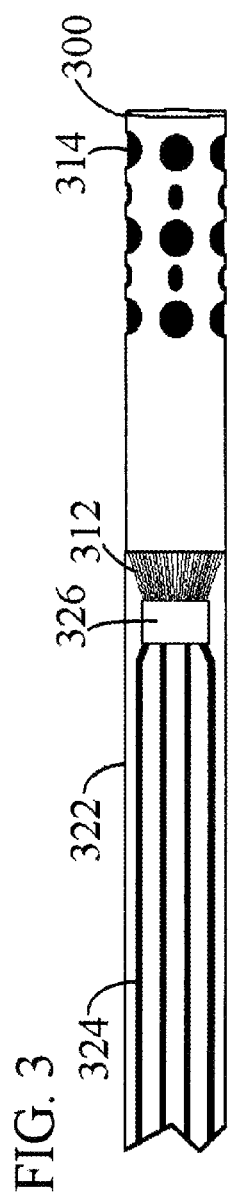
FIG. 3 schematically illustrates another electrode-bearing lead tip 300 similar to that of FIGS. 1D and 2, but wherein the lead body 322 bears fewer conductors 324, which are then switched between different electrodes 314 on the lead tip 300 by a multiplexer 326.
Figure 4B:
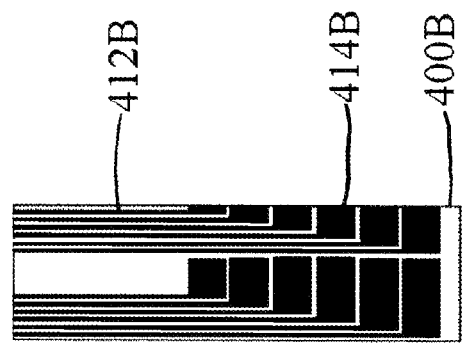
FIGS. 4A and 4B provide simplified side elevational views of the tracks 412A/412B and electrodes 414A/414B of alternative lead tips 400A and 400B (before application of an insulating coating), with the tracks 412A of FIG. 4A terminating in electrodes 414A in the form of at least substantially complete rings extending about the circumference of the lead tip 400A, and the tracks 412B of FIG. 4B terminating in electrodes 414B in the form of quarter-rings extending about the circumference of the lead tip 400B.
Figure 4A:
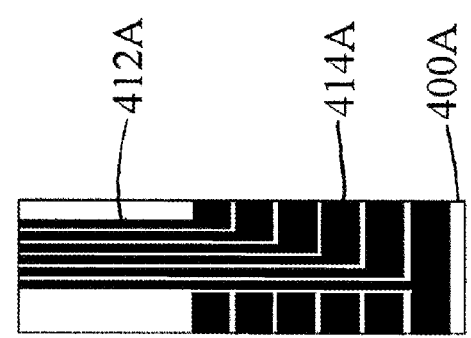

Additionally, while FIGS. 1A-1D illustrate the creation of electrodes 114, tracks 112, and track terminals 118 from a single film or layer of conductive material 110, it should be understood that these components could alternatively or additionally be formed in separate spaced layers. For example, another conductive layer could be added to the lead tip 100 of FIG. 1D (perhaps after masking the already-formed electrodes 114), followed by selective removal of the conductive layer to form additional electrodes, tracks, and/or terminals, and subsequent application of an insulating layer as desired (and removal of portions of the insulating layer, if needed to expose conductors). When conductive or insulating layers are applied, it should be understood that these need not be applied across the entire surface area of the core (or across the entirety of the spine of the lead body), and they could be applied to selected areas/surfaces. In similar respects, conductive or insulating layers can be removed as desired; for example, while an electrode may have a large area, an overlaid insulating layer may be removed over only a portion of the electrode, such that only a small area of the electrode is exposed on the surface of the lead tip.

The biocompatible and nonconductive coating used to cover the tracks, and which is then removed to expose the electrodes and terminals (or which is initially selectively applied to leave the electrodes and terminals exposed), preferably utilizes di-para-xylylene, or another poly (p-xylylene) (e,g, PARYLENE), as a starting material. The coating can be applied via chemical vapor deposition or other deposition processes, via lithography, or via other suitable application processes. When the nonconductive layer is removed to expose the electrodes, the exposed surfaces of the electrodes will typically be situated within recesses defined within a surrounding region of the nonconductive layer, as a result of the removal of the nonconductive layer to expose the electrodes. In similar respects, the conductive tracks and electrodes will typically be somewhat raised above the surface of the core. Since the conductive and nonconductive layers can be formed very thinly, typically on the order of tens to hundreds of micrometers, the variations in height along the surface of the lead are minor, which is useful to minimize trauma during insertion or removal of leads from brain tissue.

The proximal end of the lead body—which is not depicted in the accompanying drawings—may be provided with any connector suitable for connecting the lead to a neurostimulator or other medical device.

It should be understood that the versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. A method of forming a multi-electrode lead, the method including the steps of:
   a. providing an elongated core having:
      (1) a length extending between a proximal end and a distal end, and
      (2) a nonconductive exterior surface;
   b. forming conductive tracks on the core's exterior surface, wherein the step of forming the conductive tracks includes the steps of:
      i. forming a conductive layer about the core's exterior surface, and
      ii. removing portions of the conductive layer to define the conductive tracks,
      and wherein the tracks:
      (1) extending along the core's exterior surface from locations nearer the core's proximal end, and
      (2) terminating in electrodes at locations nearer the core's distal end;
   c. forming a nonconductive outer layer covering:
      (1) the tracks, except for the electrodes thereon, and
      (2) the core's exterior surface adjacent the tracks.

2. The method of claim 1 wherein the conductive tracks protrude radially from the core's exterior surface.

3. The method of claim 2 wherein the nonconductive outer layer, once formed atop the core's exterior surface and the tracks, leaves the electrodes exposed within recesses defined within a surrounding region of the nonconductive outer layer.

4. The method of claim 2 wherein the step of removing portions of the conductive layer includes one or more of:
   a. chemically etching portions of the conductive layer, and
   b. applying a laser to portions of the conductive layer, to remove the portions of the conductive layer.

5. The method of claim 1 wherein the step of forming a nonconductive outer layer includes the step of applying the nonconductive outer layer atop the core's exterior surface and the tracks, except at the electrodes, whereby the electrodes are recessed within a surrounding region of the nonconductive outer layer.

6. The method of claim 1 wherein the step of forming a nonconductive outer layer includes the steps of:
   a. applying the nonconductive outer layer atop the core's exterior surface and the tracks, and
   b. removing the nonconductive outer layer to expose the electrodes,
   whereby the electrodes are recessed within a surrounding region of the nonconductive outer layer.

7. A multi-electrode lead including:
   a. an elongated core having:
      (1) a length extending between a proximal end and a distal end, and
      (2) a nonconductive exterior surface;
   b. conductive tracks:
      (1) extending along the core's exterior surface from locations nearer the core's proximal end,
      (2) terminating in electrodes at locations nearer the core's distal end, and
      (3) being defined by removing portions of a conductive layer formed about the core's exterior surface, whereby the conductive tracks protrude radially from the core's exterior surface;
   c. a nonconductive outer layer covering:
      (1) the tracks, except for the electrodes thereon, and
      (2) the core's exterior surface adjacent the tracks.

8. The multi-electrode lead of claim 7 wherein the nonconductive outer layer is defined atop the core's exterior surface and the tracks, except at the electrodes, whereby the electrodes are recessed within a surrounding region of the nonconductive outer layer.

9. The multi-electrode lead of claim 7 wherein the electrodes are recessed within a surrounding region of the nonconductive outer layer.

10. The multi-electrode lead of claim 7 wherein:
    a. the core is at least substantially rigid, and
    b. a flexible proximal lead body is joined to the core's proximal end.

11. The multi-electrode lead of claim 10 wherein the proximal lead body has conductors extending therein, each conductor being in electrical communication with one or more of the conductive tracks.

12. The multi-electrode lead of claim 7 further including a proximal lead body having conductors extending therein, each conductor being in electrical communication with one or more of the conductive tracks.

13. The multi-electrode lead of claim 12 further including a multiplexer between the conductors and the conductive tracks, wherein the multiplexer is configured to switchably connect each conductor into electrical communication with one or more of the conductive tracks.

14. The multi-electrode lead of claim 7 wherein:
    a. the core is rigid;
    b. the conductive tracks terminate in terminals at locations nearer the core's proximal end;

c. a flexible proximal lead body is joined to the core's proximal end, the proximal lead body having conductors extending therein and connecting to the terminals.

15. The multi-electrode lead of claim 7 wherein at least some of the electrodes are spaced about a circumference of the core.

16. The multi-electrode lead of claim 7 wherein at least some of the electrodes:
   a. are spaced along the length of the core, and
   b. alternate between larger and smaller sizes along the length of the core.

17. A method of use for a multi-electrode lead, the multi-electrode lead having:
   (a) an elongated core having:
      (i) a length extending between a proximal end and a distal end, and
      (ii) a nonconductive exterior surface;
   (b) conductive tracks:
      (i) extending along the core's exterior surface from locations nearer the core's proximal end,
      (ii) terminating in electrodes at locations nearer the core's distal end, and
      (iii) being defined by removing portions of a conductive layer formed about the core's exterior surface, whereby the conductive tracks protrude radially from the core's exterior surface;
   (c) a nonconductive outer layer covering:
      (i) the tracks, except for the electrodes thereon, and
      (ii) the core's exterior surface adjacent the tracks,
   the method including the steps of:
   b. situating the electrodes within a patient's brain, and
   c. delivering electrical stimulation to the patient's brain via two or more of the electrodes.

18. The method of claim 17 further including the step of sensing electrical activity of the patient's brain via two or more of the electrodes.

19. The method of claim 17 further including the step of delivering current between different pairs of electrodes at different times.

\* \* \* \* \*